United States Patent
Leach et al.

(10) Patent No.: US 8,444,620 B2
(45) Date of Patent: May 21, 2013

(54) METHOD AND APPARATUS FOR APPLICATION OF A FLUID

(75) Inventors: Michael D. Leach, Warsaw, IN (US); Barry F. Hecker, Pierceton, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 344 days.

(21) Appl. No.: 12/832,293

(22) Filed: Jul. 8, 2010

(65) Prior Publication Data
US 2010/0274206 A1 Oct. 28, 2010

Related U.S. Application Data

(62) Division of application No. 11/222,303, filed on Sep. 8, 2005, now Pat. No. 7,766,900.

(60) Provisional application No. 60/654,720, filed on Feb. 21, 2005.

(51) Int. Cl.
*A61M 11/00* (2006.01)
*A61M 35/00* (2006.01)
*A61M 39/00* (2006.01)
*A61M 39/08* (2006.01)

(52) U.S. Cl.
USPC ........ 604/403; 604/4.01; 604/5.01; 604/6.15; 604/46; 604/289; 604/290; 604/310; 604/311; 604/416; 210/767; 210/787; 210/789; 210/790

(58) Field of Classification Search ................ 604/4.01, 604/5.01, 6.01, 6.04, 6.15, 46, 93.01, 181, 604/187, 218, 236, 289, 290, 310, 311, 540, 604/403, 416; 210/767, 787, 789, 790
See application file for complete search history.

(56) References Cited

U.S. PATENT DOCUMENTS

| | | | |
|---|---|---|---|
| 1,378,806 | A | 5/1921 | Ausubel |
| 1,948,388 | A | 2/1934 | Liberson |
| 1,950,137 | A | 3/1934 | Dowe |
| 2,112,160 | A | 3/1938 | Johnson |

(Continued)

FOREIGN PATENT DOCUMENTS

| | | |
|---|---|---|
| CA | 2244697 | 8/1997 |
| CA | 2295733 A1 | 1/1999 |

(Continued)

OTHER PUBLICATIONS

"The New Gold Standard" brochure for GPS® Mini and GPS® II Platelet Concentrate Separation Kit with ACD-A Anticoagulant, Biomet Biologics, Inc. (Dec. 2006), 7 pages.

(Continued)

*Primary Examiner* — Leslie Deak
*Assistant Examiner* — Adam Marcetich
(74) *Attorney, Agent, or Firm* — Harness, Dickey

(57) ABSTRACT

A method and apparatus for separation, concentration, and/or applying a biological or bio-engineered fluid. Generally, the fluid application device includes a sprayer body to enable the application of the fluid and a container adaptable to enable the separation of the fluid into at least a first component and a second component. The container is releasably coupled to the nozzle. The nozzle is adapted to withdraw at least one of the first component or the second component from the container after the fluid has been separated to apply the fluid to a selected site.

19 Claims, 10 Drawing Sheets

U.S. PATENT DOCUMENTS

Figure 1:
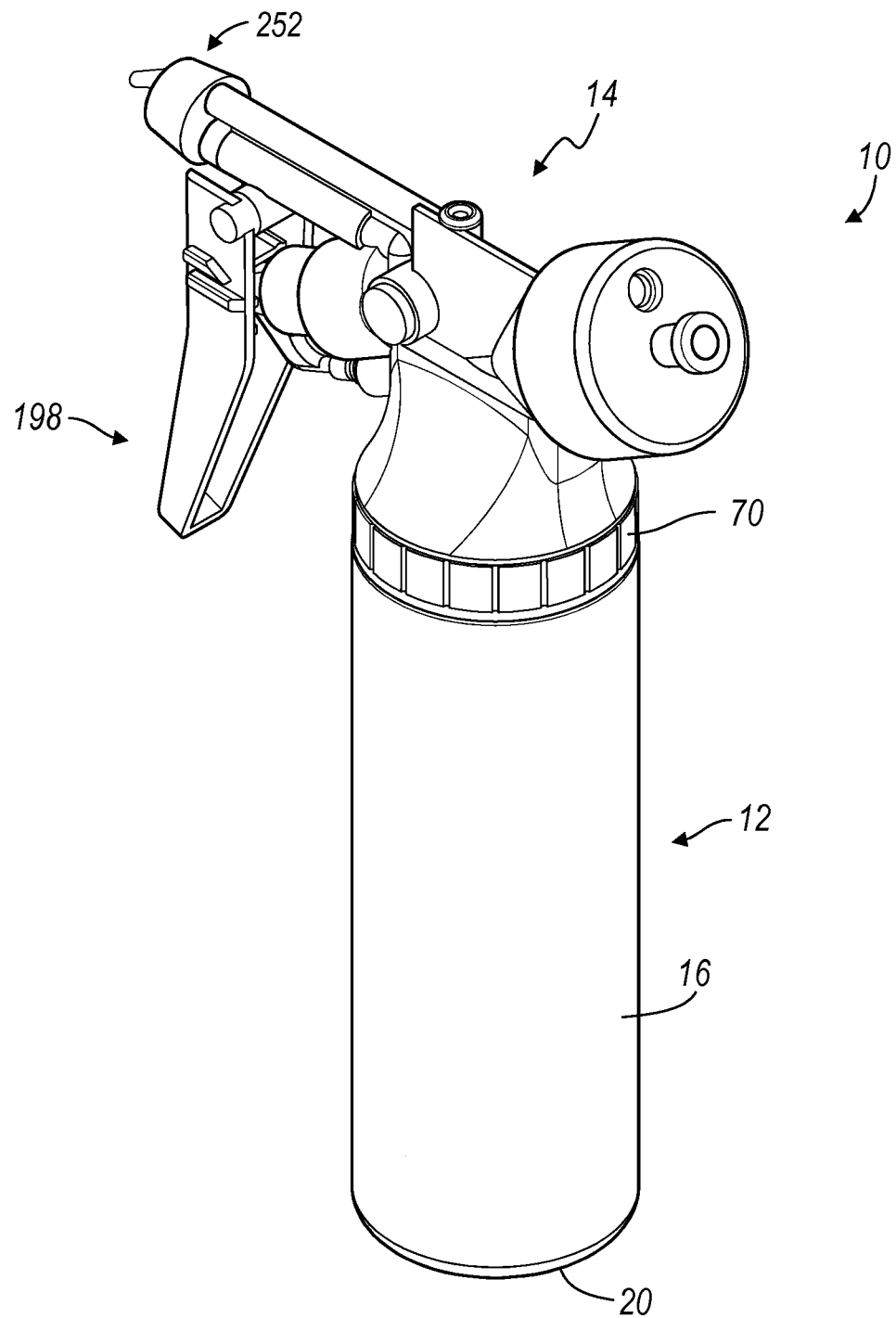

| | | |
|---|---|---|
| 2,322,753 A | 6/1943 | Thomas |
| 2,533,004 A | 12/1950 | Ferry et al. |
| 2,915,063 A | 12/1959 | Cutter |
| RE25,113 E | 1/1962 | Wilburn |
| 3,112,747 A | 12/1963 | Cowley |
| 3,215,141 A | 11/1965 | Podhora |
| 3,223,083 A | 12/1965 | Cobey |
| 3,236,418 A | 2/1966 | Dalle et al. |
| 3,314,427 A | 4/1967 | Stafford |
| 3,406,686 A | 10/1968 | Keller |
| 3,435,944 A | 4/1969 | Ishii |
| 3,467,096 A | 9/1969 | Horn |
| 3,473,646 A | 10/1969 | Burke |
| 3,552,394 A | 1/1971 | Horn |
| 3,586,064 A | 6/1971 | Brown et al. |
| 3,625,353 A | 12/1971 | Ishii |
| 3,654,925 A | 4/1972 | Holderith |
| 3,685,248 A | 8/1972 | Godelaine |
| 3,767,085 A | 10/1973 | Cannon et al. |
| 3,780,935 A | 12/1973 | Lukacs et al. |
| 3,800,947 A | 4/1974 | Smith |
| 3,828,980 A | 8/1974 | Creighton et al. |
| 3,894,952 A | 7/1975 | Ayres |
| 3,901,402 A * | 8/1975 | Ayres ............... 215/248 |
| 3,937,219 A | 2/1976 | Karakashian |
| 3,976,073 A | 8/1976 | Quick et al. |
| 4,021,352 A | 5/1977 | Sarstedt et al. |
| 4,040,420 A | 8/1977 | Speer |
| 4,046,699 A * | 9/1977 | Zine, Jr. ............ 210/516 |
| 4,057,499 A | 11/1977 | Buono |
| 4,121,739 A | 10/1978 | Devaney et al. |
| 4,142,668 A | 3/1979 | Lee |
| 4,184,593 A | 1/1980 | Dorr et al. |
| 4,202,769 A | 5/1980 | Greenspan |
| 4,226,235 A | 10/1980 | Sarnoff et al. |
| 4,260,077 A | 4/1981 | Schroeder |
| 4,269,174 A | 5/1981 | Adair |
| 4,322,298 A | 3/1982 | Persidsky |
| 4,355,739 A * | 10/1982 | Vierkotter ............ 222/134 |
| 4,359,049 A | 11/1982 | Redl et al. |
| 4,375,272 A | 3/1983 | Sutton, III |
| 4,413,773 A | 11/1983 | Rohde et al. |
| 4,424,132 A | 1/1984 | Iriguchi et al. |
| 4,434,820 A | 3/1984 | Glass |
| 4,465,476 A | 8/1984 | Gahwiler et al. |
| 4,467,588 A | 8/1984 | Carveth |
| 4,498,904 A | 2/1985 | Turner et al. |
| 4,524,770 A | 6/1985 | Orandi |
| 4,610,666 A | 9/1986 | Pizzino |
| 4,627,879 A | 12/1986 | Rose et al. |
| 4,628,969 A | 12/1986 | Jurgens, Jr. et al. |
| 4,631,055 A | 12/1986 | Redl et al. |
| 4,645,073 A * | 2/1987 | Homan ............... 206/219 |
| 4,650,468 A | 3/1987 | Jennings, Jr. |
| 4,673,395 A | 6/1987 | Phillips et al. |
| 4,714,457 A | 12/1987 | Alterbaum |
| 4,734,261 A | 3/1988 | Koizumi et al. |
| 4,735,616 A | 4/1988 | Eibl et al. |
| 4,744,955 A | 5/1988 | Shapiro |
| 4,767,026 A | 8/1988 | Keller et al. |
| 4,818,386 A | 4/1989 | Burns |
| 4,822,340 A | 4/1989 | Kamstra et al. |
| 4,826,048 A | 5/1989 | Skorka et al. |
| 4,828,716 A | 5/1989 | McEwen et al. |
| 4,874,368 A | 10/1989 | Miller et al. |
| 4,877,520 A | 10/1989 | Burns |
| 4,878,903 A | 11/1989 | Mueller |
| 4,902,281 A | 2/1990 | Avoy |
| 4,907,019 A | 3/1990 | Stephens |
| 4,932,942 A | 6/1990 | Maslanka et al. |
| 4,957,637 A | 9/1990 | Cornell |
| 4,978,336 A | 12/1990 | Capozzi et al. |
| 4,979,942 A | 12/1990 | Wolf et al. |
| 5,009,342 A * | 4/1991 | Lawrence et al. ..... 222/136 |
| 5,032,117 A | 7/1991 | Motta |
| 5,033,252 A | 7/1991 | Carter |
| 5,049,135 A | 9/1991 | Davis |
| 5,074,844 A | 12/1991 | Zdeb et al. |
| 5,080,262 A | 1/1992 | Herold et al. |
| 5,104,375 A | 4/1992 | Wolf et al. |
| 5,104,387 A | 4/1992 | Pokorney et al. |
| 5,116,315 A | 5/1992 | Capozzi et al. |
| 5,147,323 A | 9/1992 | Haber et al. |
| 5,152,905 A | 10/1992 | Pall et al. |
| 5,160,021 A | 11/1992 | Sibley et al. |
| 5,176,658 A | 1/1993 | Ranford |
| 5,217,118 A | 6/1993 | Mochizuki et al. |
| 5,226,558 A | 7/1993 | Whitney et al. |
| 5,226,877 A | 7/1993 | Epstein |
| 5,226,887 A | 7/1993 | Farr et al. |
| 5,253,785 A | 10/1993 | Haber et al. |
| 5,286,257 A | 2/1994 | Fischer |
| 5,290,259 A | 3/1994 | Fischer |
| 5,292,318 A | 3/1994 | Haber et al. |
| 5,298,024 A | 3/1994 | Richmond |
| 5,300,041 A | 4/1994 | Haber et al. |
| 5,308,041 A | 5/1994 | Griffioen et al. |
| 5,314,412 A | 5/1994 | Rex et al. |
| 5,318,524 A | 6/1994 | Morse et al. |
| 5,322,510 A | 6/1994 | Lindner et al. |
| 5,332,092 A | 7/1994 | Fischer |
| 5,354,483 A | 10/1994 | Furse |
| 5,361,906 A | 11/1994 | Sterett |
| 5,368,563 A | 11/1994 | Lonneman et al. |
| 5,372,586 A | 12/1994 | Haber et al. |
| 5,376,079 A | 12/1994 | Holm et al. |
| 5,390,792 A | 2/1995 | Van Ness et al. |
| 5,393,497 A | 2/1995 | Haber et al. |
| 5,393,674 A | 2/1995 | Levine et al. |
| 5,409,465 A | 4/1995 | Boggs et al. |
| 5,411,465 A | 5/1995 | Glen et al. |
| 5,419,491 A | 5/1995 | Breitsprecher |
| 5,420,250 A | 5/1995 | Lontz |
| 5,445,614 A | 8/1995 | Haber et al. |
| 5,454,793 A | 10/1995 | Levander et al. |
| 5,458,593 A * | 10/1995 | Macabasco et al. ......... 604/403 |
| 5,464,396 A | 11/1995 | Barta et al. |
| 5,474,540 A | 12/1995 | Miller et al. |
| 5,478,323 A | 12/1995 | Westwood et al. |
| 5,480,068 A | 1/1996 | Frazier et al. |
| 5,484,431 A | 1/1996 | Scharf et al. |
| 5,505,704 A | 4/1996 | Pawelka et al. |
| 5,510,102 A | 4/1996 | Cochrum |
| 5,519,422 A | 5/1996 | Thoman et al. |
| 5,519,931 A | 5/1996 | Reich |
| 5,520,657 A | 5/1996 | Sellers et al. |
| 5,520,658 A | 5/1996 | Holm et al. |
| 5,522,804 A | 6/1996 | Lynn |
| 5,530,531 A | 6/1996 | Girard |
| 5,542,934 A | 8/1996 | Silver |
| 5,549,651 A | 8/1996 | Lynn |
| 5,582,596 A | 12/1996 | Fukunaga et al. |
| 5,585,007 A | 12/1996 | Antanavich et al. |
| 5,597,530 A | 1/1997 | Smith et al. |
| 5,605,255 A | 2/1997 | Reidel et al. |
| 5,605,541 A | 2/1997 | Holm |
| 5,638,661 A | 6/1997 | Banks |
| 5,643,206 A | 7/1997 | Fischer |
| 5,656,035 A | 8/1997 | Avoy |
| 5,665,067 A | 9/1997 | Linder et al. |
| 5,697,915 A | 12/1997 | Lynn |
| 5,728,075 A | 3/1998 | Levander et al. |
| 5,752,626 A | 5/1998 | Bachand |
| 5,759,169 A | 6/1998 | Marx |
| 5,759,171 A | 6/1998 | Coelho et al. |
| 5,792,103 A | 8/1998 | Schwartz et al. |
| 5,810,885 A | 9/1998 | Zinger et al. |
| 5,814,022 A | 9/1998 | Antanavich et al. |
| 5,814,066 A | 9/1998 | Spotnitz |
| 5,819,988 A | 10/1998 | Sawhney et al. |
| 5,824,012 A | 10/1998 | Burchett et al. |
| 5,830,547 A | 11/1998 | MacKenzie et al. |
| 5,842,326 A | 12/1998 | Wolf |
| 5,857,591 A * | 1/1999 | Bachand ............ 222/1 |
| 5,871,700 A | 2/1999 | Konrad |
| 5,881,536 A | 3/1999 | Muller-Wille et al. |
| 5,888,408 A | 3/1999 | Nagels |

| | | | |
|---|---|---|---|
| 5,935,437 A | 8/1999 | Whitmore | |
| 5,951,517 A | 9/1999 | Lampropoulos et al. | |
| 5,964,377 A * | 10/1999 | Demarest et al. | 222/136 |
| 5,968,018 A | 10/1999 | Freeman et al. | |
| 5,976,102 A | 11/1999 | Epstein | |
| 5,980,866 A | 11/1999 | Uchida et al. | |
| 5,997,811 A | 12/1999 | Esposito | |
| 5,997,881 A | 12/1999 | Powell et al. | |
| 6,001,259 A | 12/1999 | Whitmore | |
| 6,059,749 A | 5/2000 | Marx | |
| 6,063,055 A | 5/2000 | Epstein et al. | |
| 6,079,868 A | 6/2000 | Rydell | |
| 6,099,511 A | 8/2000 | Devos et al. | |
| 6,113,571 A | 9/2000 | Zinger et al. | |
| 6,123,687 A | 9/2000 | Simonyi et al. | |
| 6,132,396 A | 10/2000 | Antanavich et al. | |
| 6,206,905 B1 | 3/2001 | Holm et al. | |
| 6,234,994 B1 | 5/2001 | Zinger et al. | |
| 6,251,370 B1 | 6/2001 | Uchida et al. | |
| 6,308,747 B1 | 10/2001 | Farris | |
| 6,328,229 B1 | 12/2001 | Duronio et al. | |
| 6,331,172 B1 | 12/2001 | Epstein et al. | |
| 6,394,982 B1 | 5/2002 | Ehrenfels | |
| 6,471,670 B1 | 10/2002 | Enrenfels et al. | |
| 6,475,193 B1 | 11/2002 | Park et al. | |
| 6,488,650 B1 | 12/2002 | Epstein et al. | |
| 6,544,162 B1 | 4/2003 | Van Wie et al. | |
| 6,648,133 B1 | 11/2003 | Blaschke et al. | |
| 6,711,879 B2 | 3/2004 | Korteweg et al. | |
| 6,830,762 B2 | 12/2004 | Baugh et al. | |
| 6,959,812 B2 | 11/2005 | Reif et al. | |
| 7,179,391 B2 | 2/2007 | Leach et al. | |
| 7,223,346 B2 | 5/2007 | Dorian et al. | |
| 7,374,678 B2 | 5/2008 | Leach et al. | |
| 7,470,371 B2 | 12/2008 | Dorian et al. | |
| 7,766,900 B2 | 8/2010 | Leach et al. | |
| 2001/0016709 A1 | 8/2001 | Tovey et al. | |
| 2002/0035820 A1 | 3/2002 | Farris | |
| 2002/0104808 A1 | 8/2002 | Blasetti et al. | |
| 2002/0185457 A1* | 12/2002 | Smith et al. | 210/787 |
| 2003/0023203 A1 | 1/2003 | Lavi et al. | |
| 2003/0029763 A1 | 2/2003 | Reif et al. | |
| 2003/0139774 A1 | 7/2003 | Epstein et al. | |
| 2003/0187408 A1* | 10/2003 | Marx | 604/236 |
| 2004/0024353 A1 | 2/2004 | Petersen et al. | |
| 2004/0035743 A1 | 2/2004 | Tighe et al. | |
| 2004/0065626 A1 | 4/2004 | Woo | |
| 2004/0209755 A1 | 10/2004 | Moore et al. | |
| 2004/0251217 A1* | 12/2004 | Leach et al. | 210/787 |
| 2005/0247715 A1 | 11/2005 | Ellsworth et al. | |
| 2006/0009713 A1* | 1/2006 | Flaherty | 600/576 |
| 2006/0064070 A1 | 3/2006 | Martin | |
| 2006/0175242 A1 | 8/2006 | Dorian et al. | |
| 2006/0196885 A1 | 9/2006 | Leach et al. | |
| 2006/0217674 A1 | 9/2006 | Romano et al. | |
| 2006/0273049 A1 | 12/2006 | Leach et al. | |
| 2006/0273050 A1 | 12/2006 | Higgins et al. | |
| 2006/0278588 A1 | 12/2006 | Woodell-May | |
| 2007/0012623 A1 | 1/2007 | Robinson et al. | |
| 2008/0217264 A1 | 9/2008 | Leach et al. | |
| 2008/0217265 A1 | 9/2008 | Leach et al. | |
| 2008/0283474 A1 | 11/2008 | Leach et al. | |
| 2009/0014391 A1 | 1/2009 | Leach et al. | |
| 2009/0221075 A1 | 9/2009 | Dorian et al. | |
| 2009/0250413 A1 | 10/2009 | Hoeppner | |
| 2009/0253566 A1 | 10/2009 | Chavarria | |

FOREIGN PATENT DOCUMENTS

| | | |
|---|---|---|
| DE | 632579 | 9/1936 |
| DE | 807113 | 6/1951 |
| DE | 3246999 A1 | 5/1984 |
| DE | 8913761 | 3/1990 |
| DE | 29516650 | 1/1996 |
| EP | 0208053 A2 | 1/1987 |
| EP | 0253418 A1 | 1/1988 |
| EP | 0253949 A2 | 1/1988 |
| EP | 0292472 | 11/1988 |
| EP | 0316284 A1 | 5/1989 |
| EP | 0432871 A2 | 6/1991 |
| EP | 0528949 A1 | 3/1993 |
| EP | 592242 | 4/1994 |
| EP | 0858776 | 8/1998 |
| FR | 840257 A | 4/1939 |
| FR | 2612782 | 9/1988 |
| FR | 2661097 | 10/1991 |
| FR | 2666986 A1 | 3/1992 |
| FR | 2668060 | 4/1992 |
| JP | 08238314 A | 9/1996 |
| JP | 08280802 A | 10/1996 |
| JP | 09108302 A | 4/1997 |
| WO | WO-8807874 | 10/1988 |
| WO | WO-9001959 | 3/1990 |
| WO | WO-9101711 | 2/1991 |
| WO | WO-9117778 A1 | 11/1991 |
| WO | WO-9419038 | 9/1994 |
| WO | WO-9639212 | 12/1996 |
| WO | WO-9725015 A1 | 7/1997 |
| WO | WO-9728834 | 8/1997 |
| WO | WO-9746203 A1 | 12/1997 |
| WO | WO-9747343 A1 | 12/1997 |
| WO | WO-9802098 | 1/1998 |
| WO | WO-9810703 | 3/1998 |
| WO | WO-9810704 | 3/1998 |
| WO | WO-9813094 | 4/1998 |
| WO | WO-9840115 | 9/1998 |
| WO | WO-9901069 | 1/1999 |
| WO | WO-03018425 A1 | 3/2003 |

OTHER PUBLICATIONS

Alving, B.M., M.J. Weinstein, et al. (1995). "Fibrin sealant: summary of a conference on characteristics and clinical uses." Transfusion 35(9): 783-90.

B. Braun/McGaw Product Catalog, May 1, 1999.

DePuy AcroMed, Inc., Symphony™ Platelet Concentrate System, 2001.

Developing Technologies for Accelerating Healing, Naturally®, Smart PReP® 2, Harvest® Technologies Corp. 2002 (6 pages).

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

DynaStat™, Introducing DynaStat™ Surgical Hemostat—An Innovation in Hemostatic Biodevices, 2000 Cohesion Technologies, Inc.

FibriJet® 11:1 Ratio Applicator, Micromedics, Inc., printed from www.micromedics-usa.com/products/PDFs/FibriJet_Easy-Assembly.pdf, in 2005 (1 page).

FibriJet® product sheet, Micromedics, Inc., printed from www.micromedics-usa.com/products/PDFs/product_sheet.pdf, in 2005 (2 pages).

FibriJet®Ratio Applicator for application of platelet gel, Micromedics, Inc., printed from www.micromedics-usa.com/products/PDFs/ratio.pdf, in 2005 (1 page).

CFT Cell Factor Technologies, Inc., GPS® II Platelet Concentrate System, 2004 Biomet Orthopedics, Inc. (10 pages).

International Preliminary Examination Report issued Oct. 5, 2010 for PCT/US2009/039488 claiming benefit of U.S. Appl. No. 12/062,817, filed Apr. 4, 2008.

International Search Report mailed Jul. 10, 2009 for PCT/US2009/039488 claiming benefit of U.S. Appl. No. 12/062,817, filed Apr. 4, 2008.

Matras, H. (1985). "Fibrin seal: the state of the art." J Oral Maxillofac Surg 43(8): 605-11.

Matras, Helene, H. P. Dinges, H. Lassmann, and B. Mamoli. "Zur nahtlosen interfaszikulären Nerventransplantation im Tierexperiment." Wein Med Woschtr 122 (37 1972): 517-523.

OEM Products Catalog, Merit® Medical, available by Jan. 2003.

Prof. H. Stütz, M.D., et al., The Use of Autologous Fibrin Glue to Reduce Perioperative Blood Loss in Total Knee Arthroplasty—Results of a Controlled Study, Translated from the original article published in Orthopädische Praxis 40, 12 (2004).

Redl, H. and G. Schlag (1986). Fibrin Sealant and Its Modes of Application. Fibrin Sealant in Operative Medicine. G. Schlad and H. Redl. Heidelberg, Springer-Verlag: 13-26.

Redl, H.G. Schlag, et al. (1982). "Methods of Fibrin Seal Application." Thorac, cardiovasc. Surgeon 30: 223-227.

Shimada, J.K. Mikami, et al. (1995). "Closure of leaks by fibrin gluing. Effects of various application techniques and temperatures." J Cardiovac Surg (Torino) 35(2): 181-4.

Sierra, D. H. "Fibrin sealant adhesive systems: a review of their chemistry, material properties and clinical applications." *J Biomater Appl* 7 (4 1993): 309-52.

Spom, L.A., et al., (1995). "Cell proliferation on fibrin: modulation by fibrinopeptide cleavage." Blood 86(5): 1802-10.

Tange, R.A. (1986). "A New Application Method for Fibrin Sealant: The Glue Gun." Fibrin Sealant in Operative Medicine. G. Schlad and H. Redl. Heidelberg, Springer-Verlag.

Vox Sanq, vol. 68: 82-89, Feb. 1995, Boomgaard et. al, Pooled Platelet Concentrates Prepared by the Platelet-Rich-Plasma Method and Filtered with Three Different Filters and Stored for 8 Days.

\* cited by examiner

METHOD AND APPARATUS FOR APPLICATION OF A FLUID

CROSS-REFERENCE TO RELATED APPLICATION

This application is a divisional of U.S. patent application Ser. No. 11/222,303 filed on Sep. 8, 2005, which claims the benefit of U.S. Provisional Application No. 60/654,720 filed on Feb. 21, 2005. The disclosures of the above applications are incorporated herein by reference.

FIELD

The present teachings relates generally to biological and bioengineered fluids, and particularly to a method and apparatus for collection, concentration, and application of such a fluid.

BACKGROUND

Various fluids, such as whole blood or various other biological fluids may be separated into their constituent parts, also referred to as fractions or phases. For example, whole blood samples may include a plurality of constituents that may be separated by density in a device such as a centrifuge. The whole blood sample may be placed in a test tube, or other similar device, which is then spun in a centrifuge. In the centrifuge the whole blood is separated into different fractions depending upon the density of that fraction. In addition, various elements may be added to the test tube to create more than two fractions. In particular, commonly used gels may be used to divide the whole blood into a plurality of different fractions which may include fractions such as buffy coat platelets, red blood cells, and plasma. Various other biological fluids may be separated as well. For example, nucleated cells may be separated and extracted from bone marrow or adipose tissue sample.

SUMMARY

A method and apparatus for collecting, concentrating, and applying a biological or bio-engineered fluid. Generally, the fluid application device includes a nozzle operable to enable the application of the fluid and a container adaptable to enable the separation of the fluid into at least a first component and a second component. The container can be releasably coupled to the nozzle. The nozzle can withdraw at least one of the first component or the second component from the container after the fluid has been separated to apply a portion of the fluid to a selected site.

A system for separating and applying a fluid is provided. The system can include a tube having a first part, a sterile container having a second part interconnected with said first part and a fluid transfer device. The tube can be removably positioned in the sterile container to maintain a sterility of a portion of the tube. The fluid transfer device can be operable to transfer a fluid into the tube while the sterility of a portion of the tube is maintained by interconnecting said fluid transfer device with said second port, and the fluid can be separated while the tube is disposed in the sterile container.

A method of separating a multi-component fluid in a container and dispensing at least one component from the container is provided. The selected component may be mixed with a second fluid. The method can include forming a first fraction and a second fraction by centrifuging the multi-component fluid disposed in the container and connecting the container to a spray assembly. The method further includes withdrawing at least a portion of the first fraction or second fraction via the spray assembly.

Also taught according to various embodiments is a method of withdrawing a material directly from a patient and collecting a selected fraction of the material for later use. The method can include filling a collection container with the material while the collection container is disposed in a sterile container. Further taught is separating the material in the collection container while the collection container is within the sterile container to form the selected fraction. Additionally, the method includes removing the collection container from the sterile container, and connecting the collection container to a spray nozzle to dispense at least the selected fraction.

Also provided in various embodiments is a nozzle assembly for dispensing a fluid. The nozzle assembly may include a first opening to communicate with a first fluid and a second opening to communicate with a second fluid. The second opening can define a passageway for the second fluid. The first opening and second opening can enable the first fluid and second fluid to mix external to the nozzle assembly.

Further areas of applicability of the present teachings will become apparent from the detailed description provided hereinafter. It should be understood that the detailed description and various examples, while indicating various embodiments, are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 1 is a perspective view of a fluid application device according to various embodiments;

FIG. 2 is an exploded view of the fluid application device of FIG. 1;

FIG. 3 is cross-sectional view of the fluid application device of FIG. 1 taken along line 3-3;

FIG. 4 is a perspective view of a kit including the fluid application device of FIG. 1;

FIG. 4A is an environmental view of the kit of FIG. 4 in use;

FIG. 4B is an environmental view of the kit of FIG. 4 in use;

FIG. 4C is a perspective view of a portion of the fluid application device in use;

FIG. 4D is a environmental view of the kit of FIG. 4 in use;

FIG. 4E is an environmental view of a final assembly of the fluid application device from the kit of FIG. 4;

FIG. 5 is an environmental view illustrating a use of the fluid application device of the present invention according to various embodiments;

FIG. 5A is a detailed environmental view of the use illustrated in FIG. 5;

FIG. 6 is a perspective view of a fluid application device according to various embodiments; and FIG. 7 is a cross sectional view of the fluid application of FIG. 6 along line 7-7.

DETAILED DESCRIPTION OF VARIOUS EMBODIMENTS

The following description of various embodiments is merely exemplary in nature and is in no way intended to limit the teachings, its application, or uses. Although the following description exemplary refers to blood separation, it will be understood that the present teachings may be used to separate and concentrate any appropriate material, such as bone marrow aspirate, adipose tissue, etc. It will be further understood that many multi-component or multi-fraction fluids may be separated. The components or fractions are generally intermingled in the whole sample but may be separated with a centrifuge device that causes increased local gravity or gravitational forces. Also, various portions, according to various embodiments, may be changed and specialized depending upon the material being separated. Although the following description will relate to the separation and application of a blood sample, it should be noted that numerous other materials could be utilized, and further, the description is understood to not limit the appended claims.

As will be discussed in more detail herein, a fluid application device 10 is taught. The fluid application device 10 includes a separating container 12 and a spray applicator 14. Both the spray applicator 14 and the separation container 12 can be provided in sterile containers that included ports to all materials to be added to them while maintaining the exterior sterility of the container. As taught further herein, the various sterile containers can include bags, rigid containers, or the like. Nevertheless, the various portions can be used to allow for the separation of a multi-component material put in a separation container 12, for use of filling the spray applicator 14 in a manner that allows for exterior sterility over the various portions. Therefore, a material can be added to the various portions of the device 10 while the exterior of the containers remain sterile so they can be easily passed into a sterile field. This can be used during a procedure when autologous materials are used so that the various portions of the device, such as the separation container 12, can be positioned in various apparati, such as a centrifuge, without requiring later sterilization of the container.

A fluid application device 10, exemplarily illustrated in FIG. 1, as described herein is configured generally to spray at least a portion of centrifuged blood mixed with a second fluid, such as a coagulant, on a selected area, such as a wound. The portion of centrifuged blood may either be platelet rich or platelet poor, depending on the application. The platelet rich blood can be applied in situations such as joint replacements, while platelet poor blood can be applied in applications such as hysterectomies. According to the various embodiments, a blood sample can be removed from the patient, centrifuged and re-applied while minimizing the components and steps necessary to apply the selected portion of the centrifuged blood. Also, the blood product or portion applied may be entirely or substantially autologous. This can decrease a chance of contamination or rejection since the patient's own blood is used. Also, the use of a single configured fat cell for most of the withdrawal, separation, mixing, and application of the portion may assist in the procedure.

Figures 2, 2A:
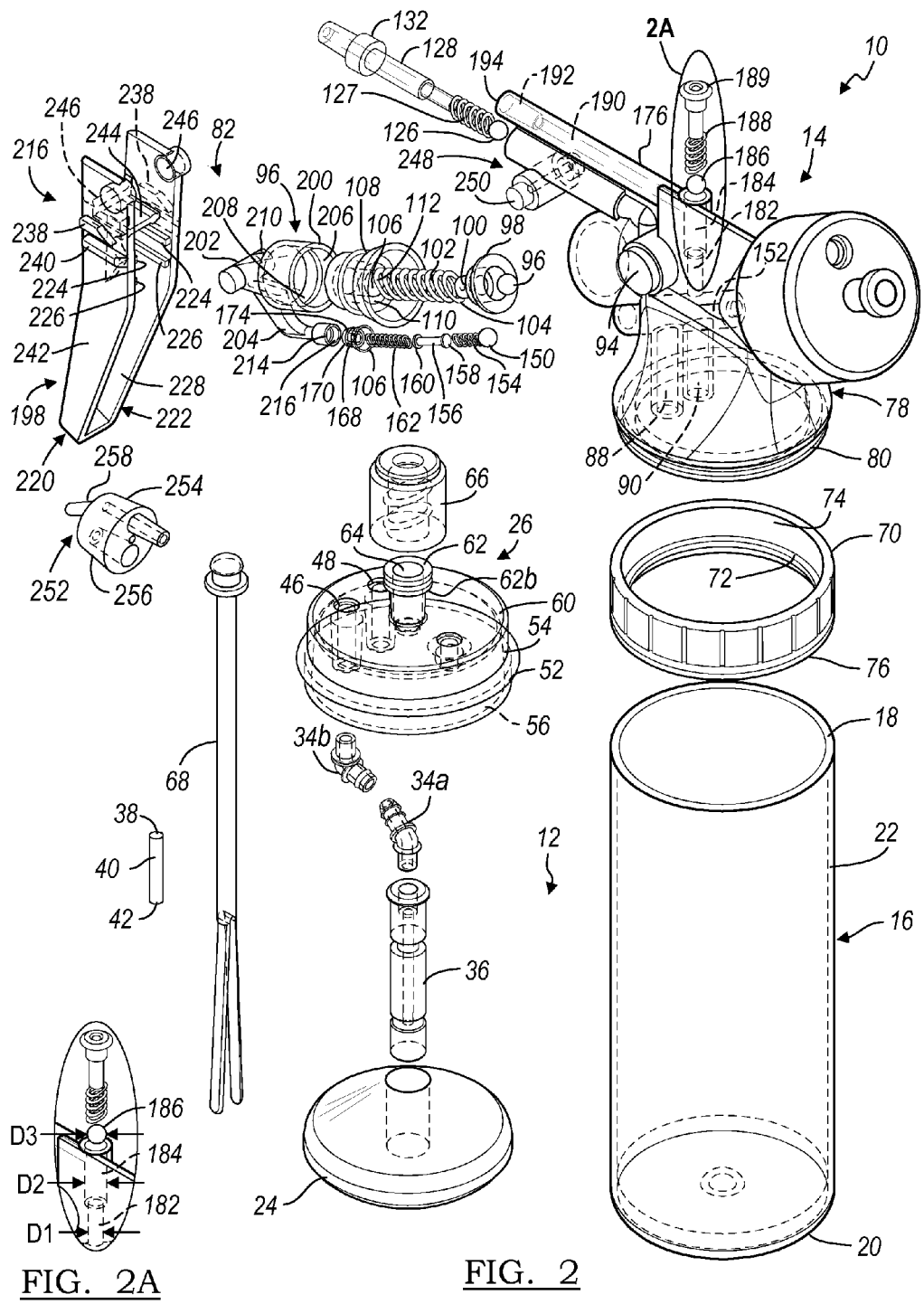
Figure 3:
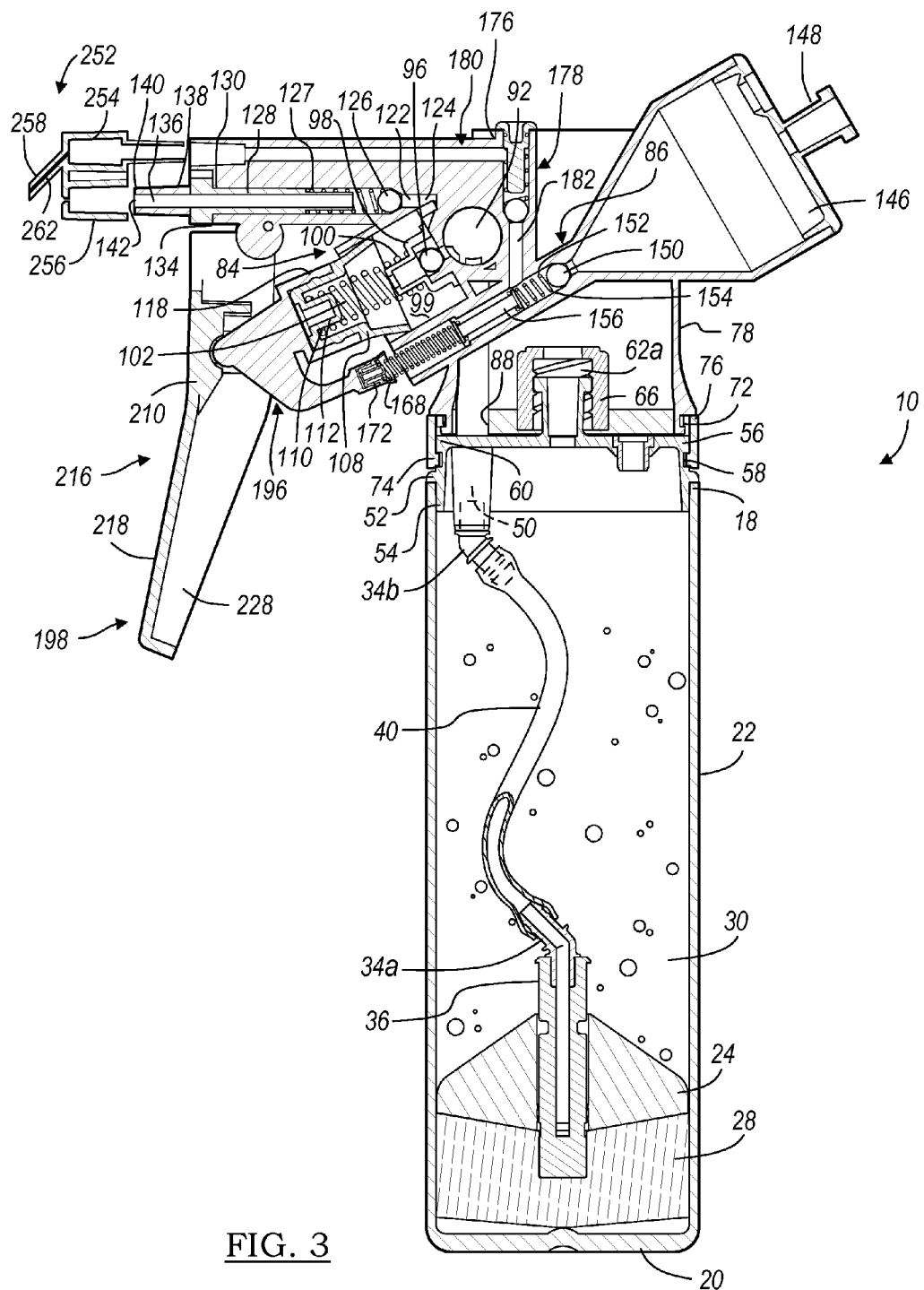

With reference to FIGS. 1, 2 and 3, a fluid application device 10 is illustrated. The fluid application device 10 includes a separator 12 and a spray applicator 14. The separator 12, according to various embodiments, is described in co-pending U.S. patent application Ser. No. 10/445,381, entitled "Apparatus and Method for Separating and Concentrating Fluids Containing Multiple Components," which is incorporated herein by reference in its entirety. In addition, the separator 12 may be the separator described in a second co-pending U.S. patent application Ser. No. 10/932,882, entitled "Apparatus and Method for Separating and Concentrating Fluids Containing Multiple Components," filed on Sep. 2, 2004 to Leach et al., which is incorporated herein by reference in its entirety. Briefly, however, the separator 12 includes a tube 16 having a top 18, a bottom 20, and a wall 22. The separator 12 further includes a buoy 24 and a cap 26. The separator 12 is configured to fit into a centrifuge (not shown) to enable the separation of a blood sample or other sample.

The separator 12 may be spun at any appropriate rate in the centrifuge, such as in a range of about 1,000 to about 8,000 RPMs. This produces a force of about 65 to about 4500 times greater than the force of normal gravity, as generally calculated in the art, on the separator 12 and the blood sample placed in the separator 12. At this force, the more dense material in a whole blood sample is forced towards a bottom 20 of the tube 16. The dense material, such as red blood cells or a red blood cell fraction 28, collects on the tube bottom 20. The buoy 24 may be formed to have a density that is less than the red blood cell fraction 28, and thus it is forced in a direction toward the top 18 of the tube 16 in the centrifuge. Nevertheless, because the buoy 24 may also be formed to be denser than a plasma fraction 30, the buoy 24 may not reach the top 18 of the tube 16.

The forces also affect the tube wall 22. The forces compress the tube 16 linearly along axis A thereby bowing or flexing the tube wall 22. As the tube wall 22 compresses it increases the diameter of the tube 16 making it easier for the buoy 24 to move in the direction of the top 18 of the tube 16. In addition, a bottom face 32 of the buoy 24 defines an inverse cone and helps the initial upward movement of the buoy 24.

During the centrifuge process, the red bloods cells of the red blood cell fraction 28 force the buoy 24 in the direction of the top 18 of the tube 16 because the buoy 24 is less dense than the red blood cell fraction 28. Although the whole blood sample, including the red blood cells, is loaded above the buoy 24, the red blood cells are able to move between the buoy 24 and the tube wall 22 because the circumference of the buoy 24 is less than the internal circumference of the tube 16 and the tube flexes during centrifuging. The difference may be any appropriate dimension to assist in moving the buoy 24, while maintaining the separation of the material. During the centrifuge process the buoy 24 stops at an interface of the plasma fraction 30 and the red blood cell fraction 28 because of the selected or tuned density of the buoy 24, although any appropriate density can be chosen for the buoy 24.

With continuing reference to FIGS. 1, 2 and 3, the buoy 24 includes a hose barb 34a coupled to a withdrawal tube 36 extending through the buoy 24. The hose barb 34a is configured to receive a first end 38 of a tube 40 that may be flexible, as best shown in FIG. 3. Although the hose barb 34a is shown, any other suitable coupler may be employed. The second end 42 of the flexible tube 40 can couple to a hose barb 34b extending from a bottom surface 44 of the cap 26.

The cap 26 serves to connect the tube 16 to the spray applicator 14. The cap 26 further includes a first outlet 46 and a second outlet 48. The first outlet 46 may comprise a formed cylindrical section 50, however, any other configuration can be used. The second outlet 48 can mate with the hose barb 34b. The first outlet 46 and second outlet 48 each extend through the cap 26. The cylindrical section 50 of the first outlet 46 is disposed within the tube 16 of the separator 12. The cylindrical section 50 on the first outlet 46 enables the withdrawal of the red blood cell fraction 28 from the tube 16 after separation of the fluid. The hose barb 34b and first and second outlets 46, 48 can be integrally formed with the cap 26 or can be fixedly attached in a post processing step, such as by adhesives. The cap 26 also includes a first annular lip 52 disposed on a side 54 of the cap 26 which interconnects the top 18 of the separator 12 to the cap 26. A second annular lip 56 on the side 54 of the cap 26 and a groove 58 created between the first and second annular lips 52, 56 enables the spray applicator 14 to be releasably attached to the cap 26, as will be described in greater detail below.

The cap 26 has a top surface 60 including a cylindrical protrusion 62 extending therefrom and including a through-bore 64. The cylindrical protrusion 62 includes a plurality of threads 62a that can mate with a nut 66 to couple the cylindrical protrusion 62 to a stabilizing rod 68 for packaging purposes, although such a stabilizing rod 68 is not necessary. The cylindrical protrusion 62 may be integrally formed with the cap 26, or may be attached to the cap 26 via an adhesive, for example.

A coupler 70 can releasably attach the spray applicator 14 to the separator 12. In particular, the coupler 70 can be annular and may include threads 72, a first annular lip 74 and a second annular lip 76 to releasably attach the cap 26 of the separator 12 to a housing 78 of the spray applicator 14. More specifically, the housing 78 of the spray applicator 14 may contain a plurality of threads 80 that are configured to mate with the threads 72 on the coupler 70. The first annular lip 74 is adapted to fit securely in the groove 58 of the cap 26, between the first and second annular lips 52, 56 of the cap 26. Although the coupler 70 can be used, according to various embodiments, other mechanisms may be used to fasten the separator 12 to the spray applicator 14, such as mechanical fasteners, a snap fit engagement mechanism, or the like. Optionally, the coupler 70 may form a vacuum seal between the spray applicator 14 and the separator 12.

The spray applicator 14 can be coupled via the cap 26 to the tube 16 to enable the withdrawal of a desired fraction of blood from the tube 16 for application of the selected blood fraction to a desired area. The spray applicator 14 includes the housing 78 and a trigger assembly 82 coupled to the housing 78. The housing 78 includes a first fluid assembly 84 and a second fluid assembly 86. The first fluid assembly 84 is coupled to the separator 12, and enables the extraction of either the red blood cell fraction 28 or plasma fraction 30 from the separator 12, as will be described in greater detail below.

The first fluid assembly 84 includes a first withdrawal tube 88 and a second withdrawal tube 90. The first withdrawal tube 88 is fluidly coupled to the first outlet 46 and the second withdrawal tube 90 is fluidly coupled to the second outlet 48. The first and second withdrawal tubes 88, 90 can be in communication with a selector valve 92. The selector valve 92 is configured to either mate with the first outlet 46 or second outlet 48 depending upon input received from a knob 94. The knob 94 is coupled to the selector valve 92 and extends outside the housing 78 of the spray applicator 14 to enable an operator of the fluid application device 10 to select the desired blood composition by using the knob 94. It should be noted that although the selector valve 92 and knob 94 may be two distinct pieces, according to various embodiments, the selector valve 92 and knob 94 can be formed as one piece.

The selector valve 92 is fluidly coupled to a first check valve 96. The first check valve 96 is retained in a first cup shaped housing 98, however any other suitable housing could be employed. The first cup shaped housing 98 is disposed in a first chamber 99. The first cup shaped housing 98 includes a bottom section 100 that is adapted to fit inside a first spring 102. The first spring 102 has a first end 104 configured for receipt of the bottom section 100 and a second end 106 configured to mate with a second cup shaped housing 108. The second cup shaped housing 108 includes a bottom section 110 that has a first cylindrical protrusion 112 adapted to mate with the second end 106 of the first spring 102. The second cup shaped housing 108 can couple the first fluid assembly 84 to the trigger assembly 82. The second cup shaped housing 108 includes an exterior ring 118 that is adapted to mate with the trigger assembly 82, as will be discussed in greater detail below.

The first fluid assembly 84 also includes an outlet 120 defined by the housing 78 and fluidly coupled to a chamber 122. In particular, the outlet 120 includes the chamber 122 at a first end 124 in which a check valve 126 is disposed. A spring 127 is positioned in the chamber 122 of the outlet 120, adjacent to the check valve 126, to provide a force to keep the check valve 126 in place.

An insert 128 is attached to a second end 130 of the outlet 120. Specifically, the insert 128 includes a ring 132 to enable the insert 128 to be pushed into the outlet 120 until the ring 132 abuts a first ridge 134 formed in the housing 78. The insert 128 further includes an interior passage 136 fluidly coupled to the chamber 122 of the outlet 120 for receipt of the selected blood composition. The insert 128 also includes a nozzle 138 having an exterior 140 and an interior 142. The exterior 140 is conical and enables the operator of the fluid application device 10 to apply the fluid close to a desired site on a patient. The interior 142 is conical in shape and creates a conical spray pattern which can improve mixing with a second fluid 144, as will be described in greater detail below. Alternatively, the interior 142 of the nozzle 138 could be cylindrical to enable pinpoint application of the first fluid. Although the outlet 120 is described according to various embodiments as distinct pieces, it shall be understood that the outlet 120 could be formed as one piece with the housing 78, and further that different configurations of the nozzle 138 may be employed.

The second fluid assembly 86 enables a second fluid to mix with the pre-selected blood from the first fluid assembly 84 in a selected ratio, such as about one to about ten. The second fluid assembly 86 includes a reservoir 146 for receipt of the second fluid. The second fluid may be any type of fluid, such as a coagulant, including a thrombin solution or the like, as will be described in greater detail below. The reservoir 146 may be formed as one piece with the housing 78 or may be a separate piece attached to the housing 78.

The reservoir 146 includes an inlet 148 for insertion of the second material therethrough. At the end of the reservoir 146 is a check valve 150 disposed in a chamber 152 coupled to or formed with the reservoir 146. The reservoir 146 and chamber 152 are generally located at an angle with respect to the separator 12, to facilitate the removal of the second fluid from the reservoir 146. A spring 154 abuts the check valve 150 to provide a force to keep the check valve 150 adjacent to the reservoir 146 and prevent the unwanted escape of the second fluid from the reservoir 146.

A stopper 156 is located in the chamber 152, and has a first end 158 adjacent to the spring 154. The stopper 156 further includes a second end 160 adjacent to a second spring 162. The first and second ends 158, 160 of the stopper 156 are generally cylindrical in shape, however, the second end 160 may be slightly larger than the first end 158 to prevent the second fluid from exiting the chamber 152.

The second spring 162 has a first end 164 that is adjacent to the second end 160 of the stopper 156 and a second end 166 which is configured to mate with a third cup shaped housing 168. The third cup shaped housing 168 includes a bottom section 170 having a first cylindrical protrusion 172 adapted to mate with the second end 166 of the second spring 162. The third cup shaped housing 168 is configured to couple the second fluid assembly 86 to the trigger assembly 82. The third cup shaped housing 168 includes an exterior ring 174 that is adapted to mate with the trigger assembly 82, as will be described in greater detail below.

The second fluid assembly 86 also includes an outlet passage 176 fluidly coupled to the chamber 152 to enable the second fluid to exit the reservoir 146. The outlet passage 176 may include a first passage 178 in fluid communication with a second passage 180. The first passage 178 intersects the chamber 152 and extends vertically therefrom, such that the first passage 178 is approximately parallel to the separator 12. The first passage 178 includes a first section 182 and a second section 184. The first section 182 is fluidly coupled to the chamber 152 and has a first diameter D1 which is smaller than a second diameter D2 of the second section 184. The second section 184 includes a check valve 186 having a diameter D3 smaller than the second diameter D2 of the second section 184, but larger than the first diameter D1 of the first section 182 to retain the check valve 186 in the second section 184. A spring 188 is disposed in the second section 184 of the first passage 178 adjacent to the check valve 186, to provide a force against the check valve 186 to prevent the fluid from exiting the first section 182 of the chamber 152. A plug 189 is further disposed in the second section 184 of the first passage 178 to seal the check valve 186 and spring 188 within the first passage 178.

The second passage 180 is fluidly coupled to the first passage 178 and includes a first chamber 190 extending substantially the length of the housing 78. The second passage 180 includes the first chamber 190 which generally intersects the first passage 178 at a selected angle and extends through the housing 78 to a second chamber 192 which is conical in shape. The second chamber 192 has an outlet 194 for dispensing the second fluid into the atmosphere.

Both the first fluid assembly 84 and the second fluid assembly 86 are each coupled to the trigger assembly 82. The trigger assembly 82 operates to control the flow of the fluids through the first fluid assembly 84 and second fluid assembly 86. The trigger assembly 82 includes a trigger connector 196 coupled to a trigger piece 198. The trigger connector 196 has a first end 200, a second end 202, and a third end 204. The first end 200 of the trigger connector 196 includes a cavity 206, which is generally cylindrical and includes an internal groove 208. The second cup shaped housing 108 of the first fluid assembly 84 is configured to interconnect and/or fit securely within the cavity 206. For example, the exterior ring 118 of the second cup shaped housing 108 may mate with the internal groove 208 of the cavity 206. The second end 202 of the trigger connector 196 includes an elongated cylinder 210 adapted to pivotably attach the trigger connector 196 to the trigger piece 198. The third end 204 includes a smaller cup shaped cavity 212 adapted to engage the second fluid assembly 86. The third cup shaped housing 168 of the second fluid assembly 86 can be configured to mate with the cavity 206 via an internal groove 214 formed in the cavity 212. In particular, the exterior ring 174 of the third cup shaped housing 168 is configured to engage the internal groove 214 of the cavity 212. Thus, both the first and second fluid assemblies 84, 86 are coupled to the trigger assembly 82 via the trigger connector 196.

The trigger piece 198 includes a housing 216 defined by a front surface 218, a left side 220 and a right side 222. The front surface 218 is generally flat to provide a surface for an operator to engage the trigger piece 198. The left and right sides 220, 222 each include a first ledge 224, and a second ledge 226 on an interior surface 228. The first and second ledges on the interior surface 228 are configured to guide the elongated cylinder 210 on the second end 228 of the trigger connector 196 into a curved piece 210 fixed to a rear surface 202 of the front surface 218. In particular, the curved piece 234 is adapted to fixedly receive the elongated cylinder 210 on the second end 228 of the trigger connector 196 and enables the elongated cylinder 210 to rotate within the curved piece 234 upon the depression of the trigger piece 198 by an operator. A first ridge 238 and a second ridge 240 are located on an exterior surface 242. The first and second ridges 238, 240 on the exterior surface 242 can provide a gripping surface. An interior plate 244 coupled to the interior surface 228 of the left and right sides 220, 222 rests against a surface 218 when the trigger piece 198 is in a first stationary position and prevents the trigger piece 198 from rotating forward.

The left and right sides 220, 222 of the trigger piece 198 each further include a cylindrical cavity 246 formed in a top section 248 of each of the left and right sides 220, 222. The cylindrical cavities 246 are adapted to mate with a plunger assembly 248 that serves to removably and rotatably attach the trigger piece 198 to the housing 78. In particular, the plunger assembly 248 includes two plungers 250, each plunger 250 is adapted to compress and then lock into place within the corresponding cylindrical cavities 246 in the left and right sides 220, 222 of the trigger piece 198. The fit of the plungers 250 in the cylindrical cavities 246 is such that it allows the trigger piece 198 to rotate when the trigger piece 198 is depressed by an operator. Thus, the first check valve 96, first cup shaped housing 98, first spring 102, second cup shaped housing 108 and trigger connector 196 enable the selected blood to enter the chamber 99 when the trigger piece 198 is depressed.

In addition, as best shown in FIGS. 2 and 3, a nozzle assembly 252 can be coupled to the first and second fluid assemblies 84, 86 to apply the first and second fluids. The nozzle assembly 252 may include a first nozzle 254 which is generally cylindrical in shape and configured to fluidly couple the first nozzle 254 to the outlet 194 of the second fluid assembly 86. A second nozzle 256 may also be included to fluidly couple the exterior 140 of the nozzle 138 of the first fluid assembly 84 to the nozzle assembly 252. In various embodiments, for example, the first nozzle 254 abuts the second fluid assembly 86, and the second nozzle 256 fits onto the exterior 140 of the nozzle 138 of the first fluid assembly 84 to hold the nozzle assembly 262 into place. The first nozzle 254 includes a first passage 258 for dripping the second fluid into the atmosphere.

Figure 5:
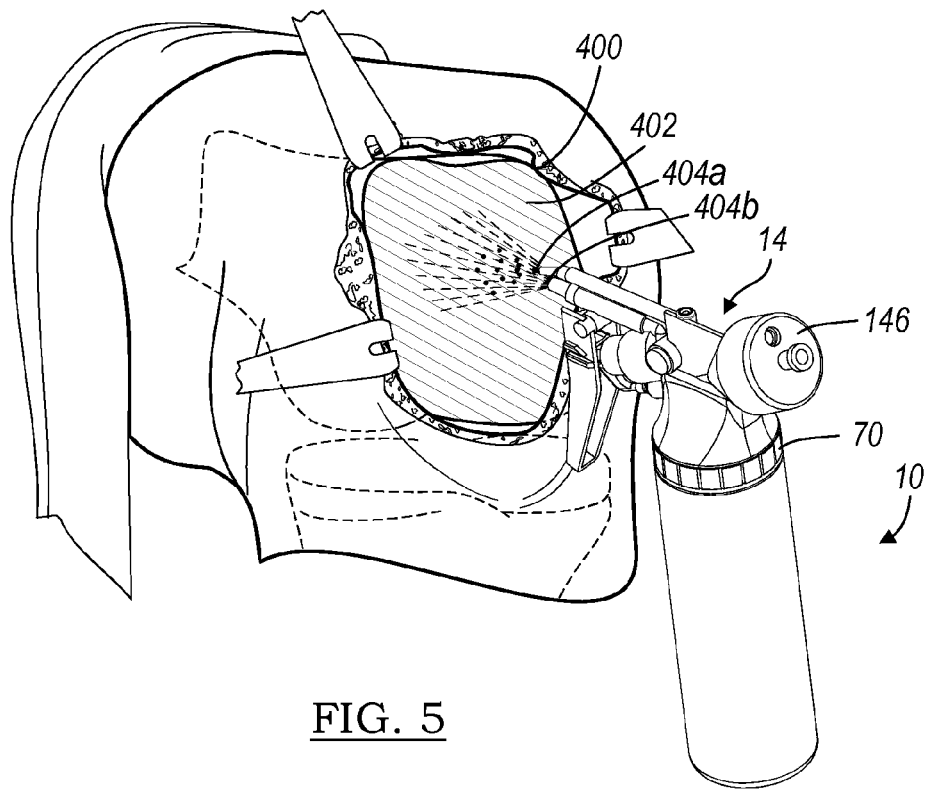
Figure 5A:
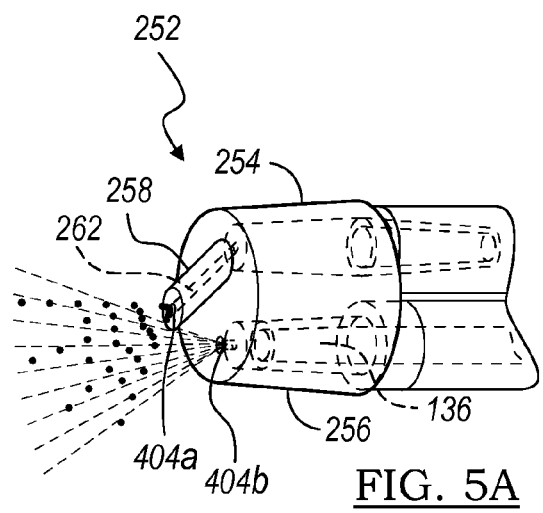

Typically, the second nozzle 256 includes an interior tapered portion 260 configured to enable the second nozzle 256 to spray the first fluid into the atmosphere in a mist, as best shown in FIG. 5A. The first passage 258 of the first nozzle 254 is generally configured to include a sloped portion 262 to enable the second fluid to drip onto the spray of the first fluid. According to various embodiments, the second fluid can drip into the atomized first fluid to enable the first and second fluid to mix external to the nozzle assembly 252. By enabling the first and second fluid to mix external to the nozzle assembly 252, the chance of the nozzle assembly 252 clogging is greatly reduced.

Figure 4:
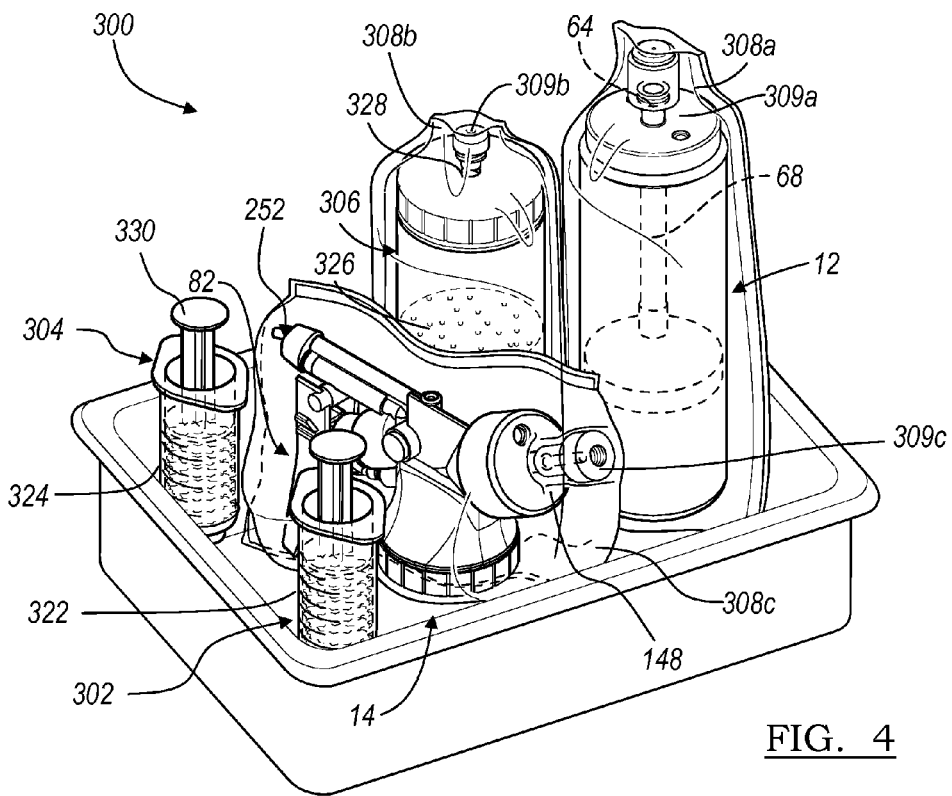

With continuing reference to FIGS. 2 and 3, with additional reference to FIG. 4, the fluid application device 10 can be a part of a kit 300. The kit 300 can include the fluid application device 10, a first syringe 302, a second syringe 304, and a vial 306. Various portions of the kit 300 can be inside at least one sterile container 308. In this kit 300, the separator 12 of the fluid application device 10 can include the stabilizing rod 68 which generally remains disposed inside of the separator 12 prior to use. The stabilizing rod 68 can protect the buoy 24 from damage during shipping. The stabilizing rod 68 is generally uncoupled from the cylindrical protrusion 62 and removed from the separator 12 to enable the insertion of a blood sample into the separator 12.

Figure 4A:
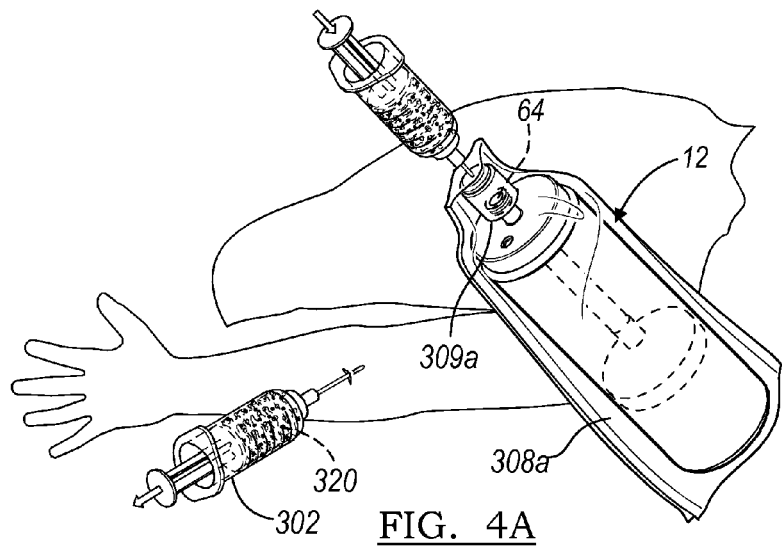
Figure 4B:
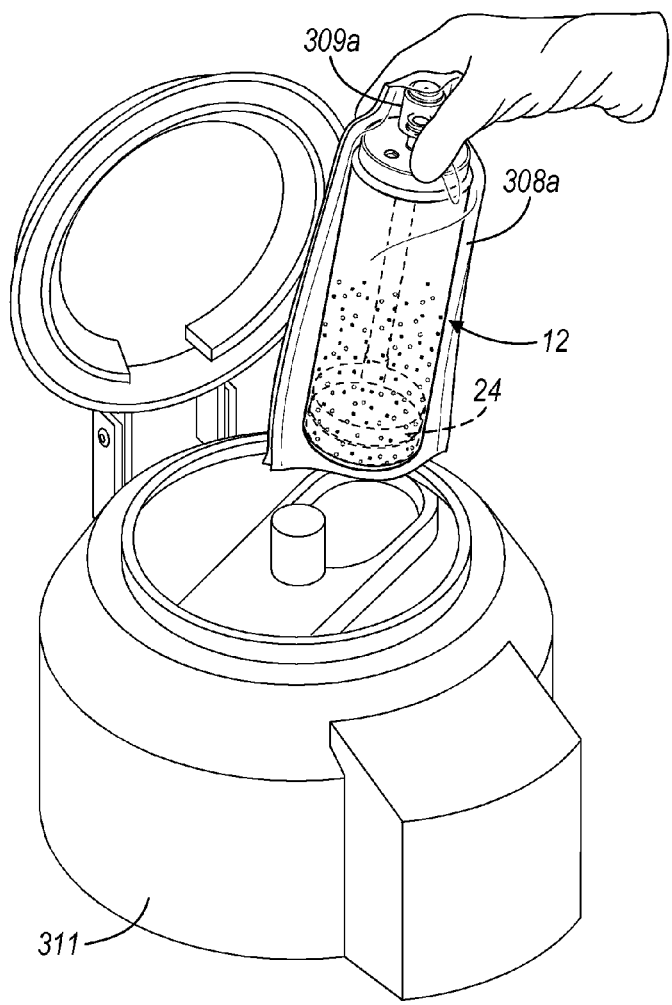

More specifically, the first syringe 302 may be used to withdraw the blood sample from a patient and may include a first fluid 320 as shown in FIG. 4A. The first fluid 320 may be an anti-coagulant, such as, for example, ADHA. The first syringe 302, once filled to a desired level with the blood sample from a patient, can then deposit the blood sample from the patient into the separator 12 that can be in a sterile container or bag 308a via a port 309a in the sterile bag 308a which is fluidly coupled to the throughbore 64 in the cap 26. Once the blood sample is in the separator 12, the separator 12 can then be transported to a centrifuge 311, as shown in FIG. 4B. The sterile bag 308a allows the separator 12 to remain sterile during centrifugation.

Figure 4C:
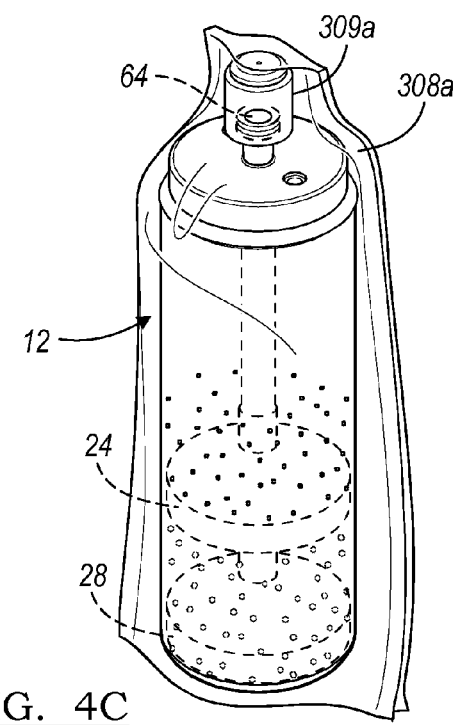
Figure 4D:
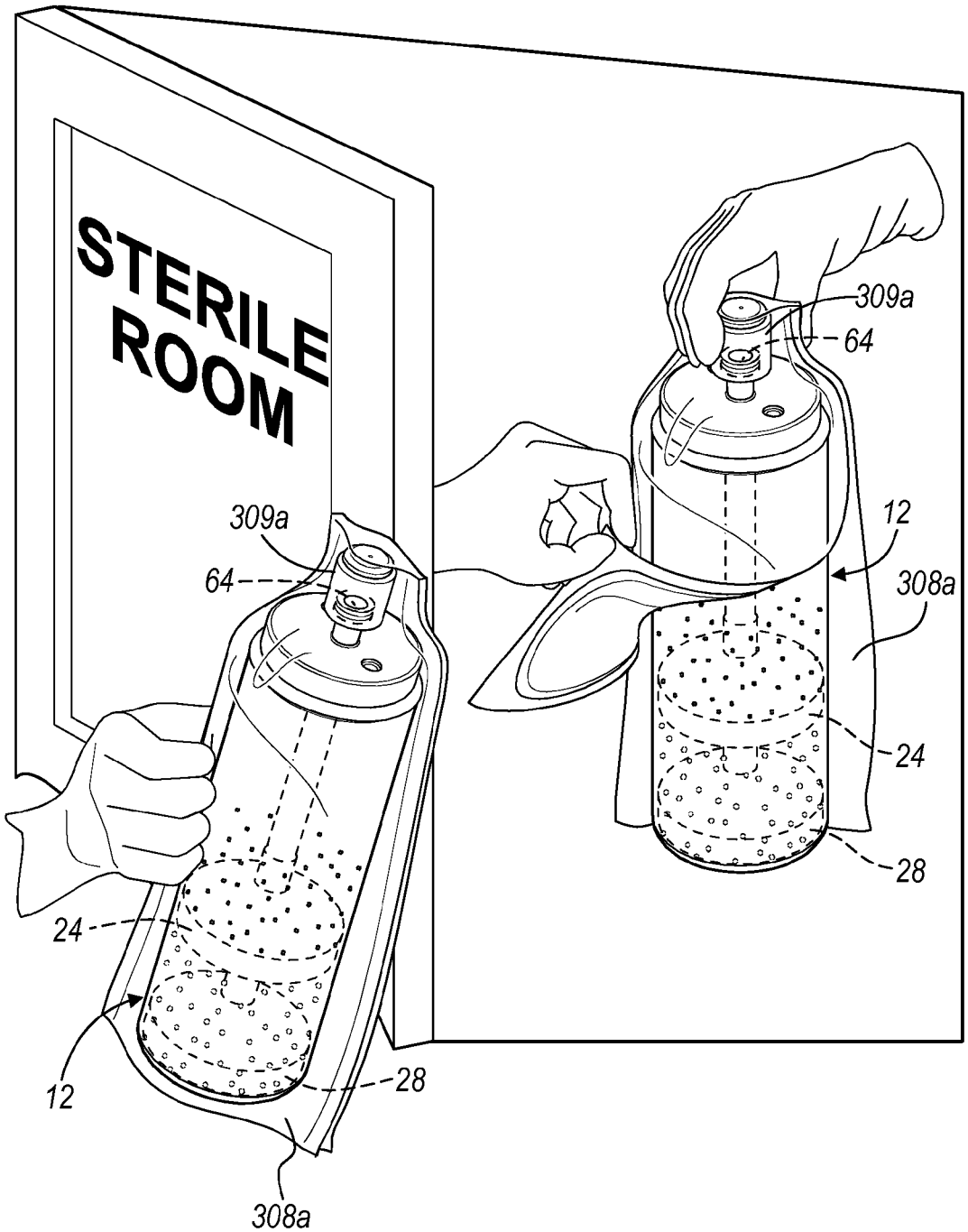
Figure 4E:

With reference now to FIG. 4C, the separator 12, disposed in the sterile bag 308a, can be removed from the centrifuge 311 after centrifugation. As illustrated, at the end of the centrifugation, the buoy 24 is disposed above the red blood cell fraction 28. As shown in FIG. 4D, the centrifuged separator 12 can be taken from the centrifuge 311 and near a sterile field to be removed from the sterile bag 308a. The separator 12 has maintained exterior sterility during centrifugation because of the sterile bag 308a. Thus, no sterilization of the container 12 is required after removing the container 12 from the sterile bag 308a.

The spray applicator 14 can also be provided in a sterile bag 308c. The sterile bag 308c can include a port 309c that can allow for introduction of a material into the reservoir 146 of the spray applicator 14. The material can be any appropriate material, such as autologous thrombin, xenographic thrombin, or other appropriate materials. If autologous thrombin is used, the material can be obtained from the patient in a substantially sterile fashion and introduced into the spray applicator 14 through the port in the sterile bag 308c. Therefore, the material that is positioned in the spray applicator 14 can also be introduced into the spray applicator 14 in a substantially sterile manner and the spray applicator 14 can be delivered near the sterile field in the sterile bag 308c also in a substantially sterile manner. Therefore, the material can be provided to the spray applicator 14 and other sterilization steps are not required.

The second syringe 304 can be used to create the second fluid. Specifically, the second syringe 304 can include a third fluid 324, such as, for example, calcium chloride ($CaCl_2$) or any other similar material which can react with a solid material 326 in the vial 306 to form a solution. The vial 306 may also be contained in a sterile bag 308b. The vial 306 may have an opening 328 that enables the receipt of the second syringe 304 therein, but prevents the escape of fluid therefrom. A plunger 330 on the second syringe 304 can then be depressed to release the third fluid 324 into the vial 306 via the port 309b on the sterile bag 308b. The vial 306 can then be shaken if necessary to mix the solid material 326 with the third fluid 324. The solid material 326 may be a clotting agent, such as, for example, thrombin. Thus, the third fluid 324 and solid material 326 may be used to make the second fluid, a thrombin solution, for example, which can then be withdrawn from the vial 306 via the port 309b on the sterile bag 308b. The second syringe 304, when filled to a desired level, can then deposit the solution of the third fluid 324 and the solid material 326 into the reservoir 146 of the spray applicator 14, through the port 309c on the sterile bag 308c. The second fluid can also be formed from a portion of the blood withdrawn from the patient or from another source, such as bovine blood.

With continuing reference to FIGS. 1, 2 and 3, and additional reference to FIG. 5, once the second fluid is in the reservoir 146 and the blood has been separated in the separator 12, the fluid application device 10 can be utilized by an operator to spray a surgical site 400 with a mixture of the first fluid and second fluid. In particular, once the trigger piece 198 is pulled backward by an operator, the first cup shaped housing 98 is pulled downward by the first spring 102, displacing the first check valve 96, and enabling either the red blood cell fraction 28 or plasma fraction 30 from the separator 12, after the whole blood is separated, to enter the chamber 99 due to the vacuum conditions in the fluid application device 10. As the selected blood fraction enters the chamber 99, due to the pressure created by the blood entering the chamber 99, the check valve 126 can be displaced in the outlet 120 and the selected blood can exit either the nozzle 138 of the insert 128 or the second nozzle 256 of the nozzle assembly 252. The conical shape of either the second nozzle 256 or the nozzle 138 of the insert 128 can cause the selected blood fraction to spray into a conical mist pattern 402 although other spray patterns may be employed depending upon the application.

As the trigger piece 198 begins to move back into its rest position, the spring 154 in the chamber 152 begins to decompress and the check valve 150 adjacent to the reservoir 146 moves to enable the second fluid to enter the chamber 152. Simultaneously, the second fluid in the chamber 152 will begin to enter into the first passage 178 of the outlet passage 176 due to the pressure differential which exists between the chamber 152 and the first passage 178. As the second fluid moves up the first passage 178, the pressure of the fluid causes the check valve 186 to move, and enables the fluid to engage the stopper 156. Once the stopper 156 is displaced, the second fluid can exit the first passage 178 and enter the second passage 180 prior to being expelled into the atmosphere via either the outlet 194 or the trough 258 of the first nozzle 254 of the nozzle assembly 252 as shown in FIG. 5A. If the second fluid is expelled by the second passage alone, the pattern will be more in the form of a mist 404a, but if it is expelled by the trough 258 of the nozzle assembly 252, the second fluid will be expelled in droplet form 404b into the conical mist 402 of the selected blood fraction. The first and second fluid assemblies 84, 86 are configured to enable the second fluid to be disposed over top of the first fluid outside of the fluid application device 10, however, the first and second fluid assemblies 84, 86 could be modified to expel the first and second fluids at different rates depending upon the desired application.

Figure 6:
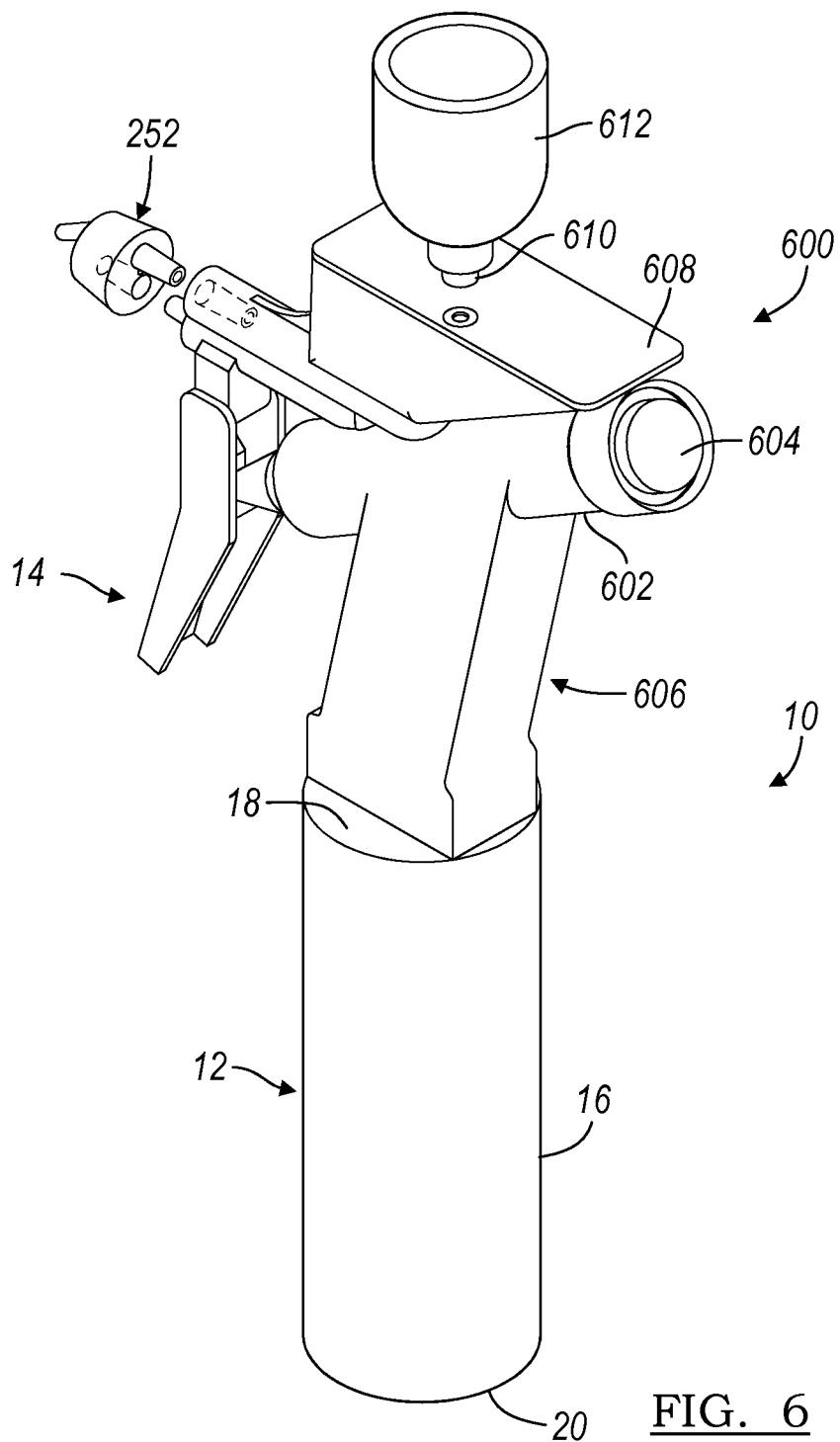
Figure 7:
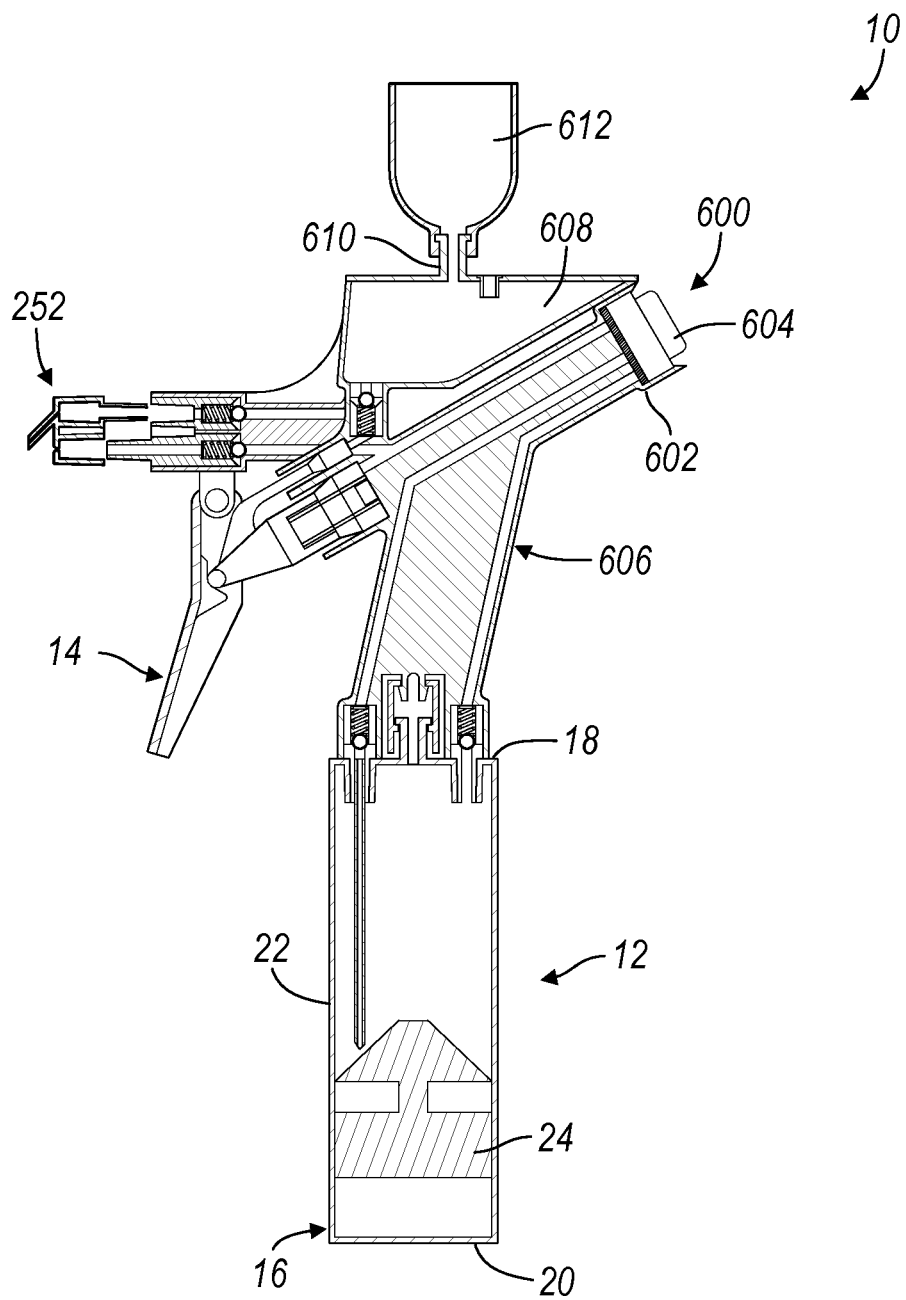

With reference now to FIGS. 6 and 7, a device according to various embodiments is shown, however, similar reference numerals will be used to denote the same or similar components. As most of the components are the same in feature and function, only those components that are substantially different will be discussed herein. The fluid application device 10 includes a selector valve 600 located at a rear end 602 of the housing 78. The selector valve 600 includes a selector knob 604 which is fluidly coupled to the red blood cell fraction 28 or plasma fraction 30 via appropriate fluid passages generally denoted as 606. The selector knob 604 upon rotation may fluidly couple either the red blood cell fraction 28 or plasma fraction 30 to the outlet 120 of the first fluid assembly 84. The outlet 120 of the first fluid assembly 84 is located adjacent the outlet passage 176 of the second fluid assembly 86. The second fluid assembly 86 includes a reservoir 608 that is disposed above the housing 78. The reservoir 606 includes a mating protrusion 610 that extends from the housing 78 and is adapted to enable a bulb shaped vial 612 to snap onto the mating protrusion 610. The bulb shaped vial 612 provides the reservoir with the second fluid, however, any other suitable mechanism could be employed.

The fluid application device 10 enables an operator to spray an operation site with either red blood cell fraction 28 or plasma fraction 30 and a coagulant prior to closing the incision. More specifically, the nozzle assembly and nozzle of the insert and outlet of the second fluid assembly enable the blood and second fluid to mix external of the fluid application device 10, which helps eliminate the chances of clogging. In addition, the ability to attach a spray applicator to a separator tube which has been centrifuged reduces the complexity of current systems which require numerous steps prior to being able to use the separated blood. In addition, the sterile bags 308a, 308b, 308c ensure the sterility of the separator 12, spray applicator 14 and vial 306 both internally and externally, and permit the centrifugation of the separator 12 while the separator 12 is maintained in the sterile bag 308a. The use of the fluid application device 10 of the present invention thus not only reduces the complexity of current systems but also increases the efficiency of the process by enabling a one step process to access the separated blood while reducing clogging.

The description of the teaching is merely exemplary in nature and, thus, variations that do not depart from the gist of the teachings are intended to be within the scope of the teachings. Such variations are not to be regarded as a departure from the spirit and scope of the teachings.

What is claimed is:

1. A device for separating and applying at least a component of a multi-component fluid, the device comprising:
    a container configured to separate the multi-component fluid into at least a first fraction and a second fraction by centrifuging;
    a spray assembly connected to the container and configured to select and apply at least a portion of the first fraction or the second fraction or both fractions; and
    wherein the spray assembly is configured to withdraw both the first and second fractions from the container while connected to the container and wherein the first and second fractions are substantially vertically spaced apart from each other in the container when selected with the spray assembly.

2. The device of claim 1 wherein the container further comprises:
    an inlet configured to receive the multi-component fluid;
    a buoy disposed in the container and configured to separate the multi-component fluid into the first fraction in a first area and the second fraction in a second area;
    a first outlet interconnecting the first area of the spray assembly; and
    a second outlet interconnecting the second area of the spray assembly.

3. The device of claim 2 wherein the spray assembly further comprises:
    a reservoir configured to receive a second fluid;
    at least one valve configured to control the release of the second fluid from the reservoir;
    a chamber configured to receive the first fraction of the multi-component fluid from the first outlet or the second fraction of the multi-component fluid from the second outlet;
    a third outlet coupled to the valve and configured to dispense the second fluid from the spray assembly;
    a fourth outlet coupled to the chamber and configured to enable the first fraction or the second fraction of the multi-component fluid to exit the spray assembly;
    a trigger coupled to the third outlet and fourth outlet; and
    wherein activation of the trigger causes the third outlet to enable the second fluid to exit the spray assembly and the fourth outlet to enable the first fraction or the second fraction of the multi-component fluid to exit the spray assembly.

4. The device of claim 3 wherein the third outlet and fourth outlet are coupled to a nozzle assembly to enable the first fraction or second fraction of the multi-component fluid to combine with the second fluid.

5. The device of claim 4 wherein the third outlet is disposed over the fourth outlet and configured such that the second fluid drips into a spray of the first fraction or second fraction of the multi-component fluid to mix after exiting the spray assembly.

6. The device of claim 3 wherein the ratio of the first fraction or second fraction of the multi-component fluid to the second fluid is approximately ten to one.

7. The device of claim 3 wherein the second fluid is a coagulant.

8. The device of claim 3 wherein the spray assembly further comprises a selector valve configured to couple the first outlet or the second outlet to the fourth outlet to transfer the first fraction or second fraction to the fourth outlet.

9. The device of claim 3 wherein activation of the trigger creates a vacuum pressure to cause the second fluid to exit the third outlet and the first fraction or second fraction of the multi-component fluid to exit the fourth outlet.

10. The device of claim 1 wherein a sterile container surrounds the container, spray assembly or both.

11. The device of claim 10 wherein the container can be used to form the first fraction and second fraction while the container is in the sterile container.

12. A system for separating and applying a multi-component fluid comprising:
    a tube having a first port;
    a sterile container having a second port interconnected with the first port; and
    a fluid transfer device; and
    a spray nozzle;
    wherein the tube is removably positioned in the sterile container to maintain a sterility of a portion of the tube;
    wherein the fluid transfer device is configured to transfer a multi-component fluid into the tube while the sterility of a portion of the tube is maintained by interconnecting the fluid transfer device with the second port;
    wherein the multi-component fluid can be separated while the tube is disposed in the sterile container;
    wherein the tube can be removed from the sterile container and coupled to the spray nozzle to apply at least a portion of either a first fraction or a second fraction of the multi-component fluid to a selected area, the first and the second fractions are substantially vertically spaced apart from each other in the tube.

13. The system of claim 12, further comprising:
    the spray nozzle having a third port;
    a second sterile container having a fourth port coupled to the third port;
    a second fluid transfer device; and
    wherein the second fluid transfer device is configured to transfer fluid into the spray nozzle through the fourth port while maintaining the sterility of the spray nozzle.

14. A device for separating and applying at least a component of a multi-component fluid, the device comprising:
    a container configured to separate the multi-component fluid into at least a first fraction and a second fraction by centrifuging;
    a buoy disposed in the container and configured to separate the multi-component fluid into the first fraction in a first area and the second fraction in a second area;
    a spray assembly connected to the container and configured to select and withdraw and apply at least a portion of the first fraction or the second fraction or both fractions, and wherein the first and second fractions are substantially vertically spaced apart from each other in the container when selected with the spray assembly;
a first outlet interconnecting the first area; and
a second outlet interconnecting the second area.

15. The device of claim 14, further comprising:
a reservoir configured to receive a second fluid; and
a check valve configured to control the release of the second fluid from the reservoir.

16. The device of claim 15, further comprising:
a chamber configured to receive the first fraction of the multi-component fluid from the first outlet or the second fraction of the multi-component fluid from the second outlet;
a third outlet coupled to the valve and configured to enable the second fluid to exit the spray assembly; and
a fourth outlet coupled to the chamber and to enable the first fraction or the second fraction of the multi-component fluid to exit the spray assembly.

17. The device of claim 16, further comprising:
a trigger coupled to the third outlet and fourth outlet, wherein when the container is filled with the first and second fluids, the trigger is configured such that activating the trigger dispenses the second fluid from the third outlet of the spray assembly and dispenses the first fraction or the second fraction of the multi-component fluid from the fourth outlet of the spray assembly.

18. The device of claim 17, further comprising:
a selector valve configured to couple the first outlet or the second outlet to the fourth outlet to enable the first fraction or second fraction to enter the fourth outlet.

19. The device of claim 17, further comprising a plunger assembly removably and rotatably coupling the trigger to a housing of the spray assembly.

* * * * *

UNITED STATES PATENT AND TRADEMARK OFFICE
CERTIFICATE OF CORRECTION

Page 1 of 3

PATENT NO. : 8,444,620 B2
APPLICATION NO. : 12/832293
DATED : May 21, 2013
INVENTOR(S) : Michael D. Leach et al.

It is certified that error appears in the above-identified patent and that said Letters Patent is hereby corrected as shown below:

On the Title Page

Item 56 References Cited, Other Publications, Column 2, line 1, Delete "B.M., M.J." and insert --B. M., M. J.--.

Item 56 References Cited, Other Publications, Column 2, line 5, Delete "Platelet" and insert --"Platelet--.

Item 56 References Cited, Other Publications, Column 2, line 5, Delete "System," and insert --System,"--.

Item 56 References Cited, Other Publications, Column 2, line 7, Delete "Developing" and insert --"Developing--.

Item 56 References Cited, Other Publications, Column 2, line 7, Delete "Healing," and insert --Healing,"--.

Item 56 References Cited, Other Publications, Column 2, line 12, Delete "Surgical" and insert --"Surgical--.

Item 56 References Cited, Other Publications, Column 2, line 13, Delete "Biodevices," and insert --Biodevices,"--.

Item 56 References Cited, Other Publications, Column 2, line 23, Delete "Platelet" and insert --"Platelet--.

Item 56 References Cited, Other Publications, Column 2, line 24, Delete "System," and insert --System,"--.

Signed and Sealed this
Tenth Day of February, 2015

Michelle K. Lee
*Deputy Director of the United States Patent and Trademark Office*

CERTIFICATE OF CORRECTION (continued)
U.S. Pat. No. 8,444,620 B2

Item 56 References Cited, Other Publications, Column 2, line 26, Delete "PCT/US2009/039488" and insert --PCT/US2009/039488,--.

Item 56 References Cited, Other Publications, Column 2, line 34, Delete "Nerventransplantation" and insert --Neuren-transplantation--.

Item 56 References Cited, Other Publications, Column 2, line 37, Delete "The" and insert --"The--.

Item 56 References Cited, Other Publications, Column 2, line 38, Delete "Arthroplasty" and insert --Arthroplasty"--.

Item 56 References Cited, Other Publications, Column 1, line 1, Delete "Fibrin" and insert --"Fibrin--.

Item 56 References Cited, Other Publications, Column 1, line 2, Delete "Application." and insert --Application."--.

Item 56 References Cited, Other Publications, Column 1, line 4, Delete "H.G." and insert --H. and G.--.

Item 56 References Cited, Other Publications, Column 1, line 6, Delete "J.K." and insert --J. and K.--.

Item 56 References Cited, Other Publications, Column 1, line 9, Delete "H." and insert --H.,--.

Item 56 References Cited, Other Publications, Column 2, line 1, Delete "L.A., et al.," and insert --L. A. et al.--.

Item 56 References Cited, Other Publications, Column 2, line 3, Delete "R.A." and insert --R. A.--.

Item 56 References Cited, Other Publications, Column 2, line 6, Delete "et. al," and insert --et al.,--.

Item 56 References Cited, Other Publications, Column 2, line 6, Delete "Pooled" and insert --"Pooled--.

Item 56 References Cited, Other Publications, Column 2, line 8, Delete "Days." and insert --Days."--.

In the Drawings

Sheet 2, Reference No. 62b, FIG. 2, Delete "62b" and insert --62a--.

Sheet 4, Reference No. 322, FIG. 4, Delete "322" and insert --320--.

CERTIFICATE OF CORRECTION (continued)
U.S. Pat. No. 8,444,620 B2

In the Specification

Column 1, Line 8, Delete "11/222,303" and insert --11/222,303,--.

Column 1, Line 9, Delete "60/654,720" and insert --60/654,720,--.

Column 1, Line 9, Delete "248" and insert --238--.

Column 1, Line 36, Delete "262" and insert --252--.

Column 1, Line 47, Delete "206" and insert --212--.

Column 1, Line 56, Delete "606" and insert --608--.

Column 1, Line 60, Delete "228" and insert --202--.

Column 1, Line 61, Delete "210" and insert --234--.

Column 1, Line 64, Delete "228" and insert --202--.